United States Patent
Carr et al.

(10) Patent No.: US 7,132,511 B2
(45) Date of Patent: Nov. 7, 2006

(54) MODIFIED ANTI-EGFR ANTIBODIES WITH REDUCED IMMUNOGENICITY

(75) Inventors: Francis J. Carr, Balmedie (GB); Graham Carter, By Newmachar (GB); Tim Jones, Babraham (GB); Stephen Williams, Auchleven Insch (GB); Anita Hamilton, Aberdeen (GB)

(73) Assignee: Merck Patent GmbH, Darmstadt (DE)

( * ) Notice: Subject to any disclaimer, the term of this patent is extended or adjusted under 35 U.S.C. 154(b) by 336 days.

(21) Appl. No.: 10/468,528

(22) PCT Filed: Feb. 18, 2002

(86) PCT No.: PCT/EP02/01687

§ 371 (c)(1),
(2), (4) Date: Aug. 19, 2003

(87) PCT Pub. No.: WO02/066058

PCT Pub. Date: Aug. 29, 2002

(65) Prior Publication Data

US 2004/0096442 A1    May 20, 2004

(30) Foreign Application Priority Data

Feb. 19, 2001 (EP) ................................. 01103954

(51) Int. Cl.
*C12P 21/08* (2006.01)

(52) U.S. Cl. ............... 530/387.3; 530/388.22; 530/330; 530/23.53; 530/329; 424/130.1; 424/133.1; 424/133.8; 424/143.1; 435/69.6; 435/172.3; 435/70.21; 435/71.1; 435/328; 435/69.7

(58) Field of Classification Search ............. 424/130.1, 424/133.1, 133.8, 143.1; 435/69.6, 172.3, 435/70.21, 71.1, 328, 69.7; 530/387.3, 388.22, 530/23.53, 329, 330

See application file for complete search history.

(56) References Cited

U.S. PATENT DOCUMENTS

| 5,558,864 | A | * | 9/1996 | Bendig et al. ............ 424/133.1 |
| 5,712,120 | A | * | 1/1998 | Rodriguez et al. .......... 435/69.6 |
| 5,891,996 | A | * | 4/1999 | Mateo de Acosta del Rio et al. ...................... 530/387.3 |

FOREIGN PATENT DOCUMENTS

| WO | WO 96/40210 | * | 12/1996 |
| WO | WO 98/52976 | * | 11/1998 |

OTHER PUBLICATIONS

Rudikoff et al (Proc Natl Acad Sci USA 1982 vol. 79 p. 1979).*

* cited by examiner

*Primary Examiner*—Larry R. Helms
*Assistant Examiner*—Parithosh K. Tungaturthi
(74) *Attorney, Agent, or Firm*—Olson & Hierl, Ltd.

(57) ABSTRACT

The present invention relates to antibodies which are directed to the EGF receptor (HER1) to be administered especially to humans and in particular for therapeutic use in tumors. The antibodies are modified whereby the modification results in a reduced propensity for the antibody to elicit an immune response upon administration to the human subject. The invention in particular relates to the modification of anti-EGFR antibody 425 in its different forms and fragments thereof to result in Mab 425 variants that are substantially non-immunogenic or less immunogenic than any non-modified counterpart when used in vivo.

3 Claims, No Drawings

SEQUENCE LISTING

<160> NUMBER OF SEQ ID NOS: 16

<210> SEQ ID NO 1
<211> LENGTH: 121
<212> TYPE: PRT
<213> ORGANISM: Artificial Sequence
<220> FEATURE:
<223> OTHER INFORMATION: Antibody fragment

<400> SEQUENCE: 1

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser His
            20                  25                  30

Trp Met His Trp Val Lys Gln Arg Ala Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
        115                 120

<210> SEQ ID NO 2
<211> LENGTH: 106
<212> TYPE: PRT
<213> ORGANISM: Artificial Sequence
<220> FEATURE:
<223> OTHER INFORMATION: Antibody fragment

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

```
Asp Ala Ala Thr Tyr Tyr Cys Gln Gln Trp Ser Ser His Ile Phe Thr
                85                  90                  95

Phe Gly Ser Gly Thr Lys Leu Glu Ile Lys
            100                 105

<210> SEQ ID NO 3
<211> LENGTH: 121
<212> TYPE: PRT
<213> ORGANISM: Artificial Sequence
<220> FEATURE:
<223> OTHER INFORMATION: Antibody fragment

<400> SEQUENCE: 3

Gln Val Gln Leu Val Gln Ser Gly Ala Glu Leu Val Lys Pro Gly Ala
1               5                   10                  15

Ser Val Lys Leu Ser Cys Lys Ala Ser Gly Tyr Thr Phe Thr Ser His
            20                  25                  30

Trp Met His Trp Val Lys Gln Ala Ala Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Arg Ala Thr Leu Thr Val Asp Lys Ser Thr Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
        115                 120

<210> SEQ ID NO 4
<211> LENGTH: 106
<212> TYPE: PRT
<213> ORGANISM: Artificial Sequence
<220> FEATURE:
<223> OTHER INFORMATION: Antibody fragment

<400> SEQUENCE: 4

Gln Ile Val Leu Thr Gln Ser Pro Ala Thr Leu Ser Ala Ser Pro Gly
1               5                   10                  15

Glu Arg Ala Thr Met Ser Cys Ser Ala Ser Ser Ser Val Thr Tyr Met
            20                  25                  30

Tyr Trp Tyr Gln Gln Lys Pro Gly Gln Ser Pro Arg Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Thr Leu Thr Ile Ser Ser Leu Glu Ala Glu
65                  70                  75                  80

Asp Ala Ala Thr Tyr Tyr Cys Gln Gln Trp Ser Ser His Ile Phe Thr
                85                  90                  95

Phe Gly Gln Gly Thr Lys Leu Glu Ile Lys
            100                 105

<210> SEQ ID NO 5
<211> LENGTH: 121
<212> TYPE: PRT
<213> ORGANISM: Artificial Sequence
<220> FEATURE:
<223> OTHER INFORMATION: Antibody fragment
```

<400> SEQUENCE: 5

```
Gln Val Gln Leu Val Gln Ser Gly Ala Glu Leu Val Lys Pro Gly Ala
 1               5                  10                  15

Ser Val Lys Leu Ser Cys Lys Ala Ser Gly Tyr Thr Phe Thr Ser His
            20                  25                  30

Trp Met His Trp Val Lys Gln Ala Pro Gly Gln Gly Pro Glu Trp Ala
        35                  40                  45

Gly Glu Phe Asn Pro Ser Asn Gly Arg Thr Asn Tyr Asn Glu Lys Phe
    50                  55                  60

Lys Ser Arg Val Thr Ile Thr Val Asp Lys Ser Thr Ser Thr Ala Tyr
 65                  70                  75                  80

Met Gln Leu Ser Ser Leu Thr Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
                100                 105                 110

Gln Gly Thr Thr Leu Thr Val Ser Ser
            115                 120
```

<210> SEQ ID NO 6
<211> LENGTH: 104
<212> TYPE: PRT
<213> ORGANISM: Artificial Sequence
<220> FEATURE:
<223> OTHER INFORMATION: Antibody fragment

<400> SEQUENCE: 6

```
Gln Ile Val Leu Thr Gln Ser Pro Ala Thr Leu Ser Ala Ser Pro Gly
 1               5                  10                  15

Glu Arg Ala Thr Met Ser Cys Ser Ala Ser Ser Ser Val Thr Tyr Met
            20                  25                  30

Tyr Trp His Gln Gln Lys Pro Gly Gln Ser Pro Arg Leu Leu Ile Tyr
        35                  40                  45

Asp Asn Leu Ala Ser Gly Val Pro Ala Arg Phe Ser Gly Ser Gly Ser
    50                  55                  60

Gly Thr Ser Tyr Thr Leu Thr Ile Ser Ser Leu Glu Ala Glu Asp Ala
 65                  70                  75                  80

Ala Thr Tyr Tyr Cys Gln Gln Trp Ser Ser His Pro Phe Thr Phe Gly
                85                  90                  95

Gln Gly Thr Lys Val Glu Ile Lys
                100
```

<210> SEQ ID NO 7
<211> LENGTH: 121
<212> TYPE: PRT
<213> ORGANISM: Artificial Sequence
<220> FEATURE:
<223> OTHER INFORMATION: Antibody fragment

<400> SEQUENCE: 7

```
Gln Val Gln Leu Val Gln Ser Gly Ala Glu Leu Val Lys Pro Gly Ala
 1               5                  10                  15

Ser Val Lys Leu Ser Cys Lys Ala Ser Gly Tyr Thr Phe Thr Ser His
            20                  25                  30

Trp Met His Trp Val Lys Gln Ala Pro Gly Gln Gly Pro Glu Trp Ile
        35                  40                  45

Gly Glu Phe Asn Pro Ser Asn Gly Arg Thr Asn Tyr Asn Glu Lys Phe
    50                  55                  60
```

```
Lys Ser Arg Val Thr Ile Thr Val Asp Lys Ser Thr Ser Thr Ala Tyr
 65                  70                  75                  80

Met Gln Leu Ser Ser Leu Thr Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
            115                 120

<210> SEQ ID NO 8
<211> LENGTH: 106
<212> TYPE: PRT
<213> ORGANISM: Artificial Sequence
<220> FEATURE:
<223> OTHER INFORMATION: Antibody fragment

<400> SEQUENCE: 8

Gln Ile Val Leu Thr Gln Ser Pro Ala Thr Leu Ser Ala Ser Pro Gly
 1               5                  10                  15

Glu Arg Ala Thr Met Ser Cys Ser Ala Ser Ser Ser Val Thr Tyr Met
                 20                  25                  30

Tyr Trp His Gln Gln Lys Pro Gly Gln Ser Pro Arg Ala Leu Ile Tyr
             35                  40                  45

Asp Thr Ser Asn Leu Ala Ser Gly Val Pro Ala Arg Phe Ser Gly Ser
 50                  55                  60

Gly Ser Gly Thr Ser Tyr Thr Leu Thr Ile Ser Ser Leu Glu Ala Glu
 65                  70                  75                  80

Asp Ala Ala Thr Tyr Tyr Cys Gln Gln Trp Ser Ser His Pro Phe Thr
                 85                  90                  95

Phe Gly Gln Gly Thr Lys Val Glu Ile Lys
            100                 105

<210> SEQ ID NO 9
<211> LENGTH: 121
<212> TYPE: PRT
<213> ORGANISM: Artificial Sequence
<220> FEATURE:
<223> OTHER INFORMATION: Antibody fragment

<400> SEQUENCE: 9

Gln Val Gln Leu Val Gln Ser Gly Ala Glu Leu Val Lys Pro Gly Ala
 1               5                  10                  15

Ser Val Lys Leu Ser Cys Lys Ala Ser Gly Tyr Thr Phe Thr Ser His
                 20                  25                  30

Trp Met His Trp Val Lys Gln Ala Pro Gly Gln Gly Leu Glu Trp Ile
             35                  40                  45

Gly Glu Phe Asn Pro Ser Asn Gly Arg Thr Asn Tyr Asn Glu Lys Phe
 50                  55                  60

Lys Ser Arg Val Thr Ile Thr Val Asp Lys Ser Thr Ser Thr Ala Tyr
 65                  70                  75                  80

Met Gln Leu Ser Ser Leu Thr Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
            115                 120

<210> SEQ ID NO 10
```

```
<211> LENGTH: 106
<212> TYPE: PRT
<213> ORGANISM: Artificial Sequence
<220> FEATURE:
<223> OTHER INFORMATION: Antibody fragment

<400> SEQUENCE: 10

Gln Ile Val Leu Thr Gln Ser Pro Ala Thr Leu Ser Ala Ser Pro Gly
1               5                   10                  15

Glu Arg Ala Thr Met Ser Cys Ser Ala Ser Ser Ser Val Thr Tyr Met
            20                  25                  30

Tyr Trp His Gln Gln Lys Pro Gly Gln Ser Pro Arg Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Thr Leu Thr Ile Ser Ser Leu Glu Ala Glu
65                  70                  75                  80

Asp Ala Ala Thr Tyr Tyr Cys Gln Gln Trp Ser Ser His Pro Phe Thr
                85                  90                  95

Phe Gly Gln Gly Thr Lys Val Glu Ile Lys
            100                 105

<210> SEQ ID NO 11
<211> LENGTH: 121
<212> TYPE: PRT
<213> ORGANISM: Artificial Sequence
<220> FEATURE:
<223> OTHER INFORMATION: Antibody fragment

<400> SEQUENCE: 11

Gln Val Gln Leu Val Gln Ser Gly Ala Glu Leu Val Lys Pro Gly Ala
1               5                   10                  15

Ser Val Lys Leu Ser Cys Lys Ala Ser Gly Tyr Thr Phe Thr Ser His
            20                  25                  30

Trp Met His Trp Val Lys Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Arg Ala Thr Leu Thr Val Asp Lys Ser Thr Ser Thr Ala Tyr
65                  70                  75                  80

Met Gln Leu Ser Ser Leu Thr Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Thr Val Ser Ser
        115                 120

<210> SEQ ID NO 12
<211> LENGTH: 106
<212> TYPE: PRT
<213> ORGANISM: Artificial Sequence
<220> FEATURE:
<223> OTHER INFORMATION: Antibody fragment

<400> SEQUENCE: 12

Gln Ile Val Leu Thr Gln Ser Pro Ala Thr Leu Ser Ala Ser Pro Gly
1               5                   10                  15

Glu Arg Ala Thr Met Ser Cys Ser Ala Ser Ser Ser Val Thr Tyr Met
            20                  25                  30
```

```
Tyr Trp His Gln Gln Lys Pro Gly Gln Ser Pro Arg Leu Leu Ile Tyr
            35                  40                  45

Asp Thr Ser Asn Leu Ala Ser Gly Val Pro Ala Arg Phe Ser Gly Ser
        50                  55                  60

Gly Ser Gly Thr Ser Tyr Thr Leu Thr Ile Ser Ser Leu Glu Ala Glu
65                  70                  75                  80

Asp Ala Ala Thr Tyr Tyr Cys Gln Gln Trp Ser Ser His Ile Phe Thr
                85                  90                  95

Phe Gly Gln Gly Thr Lys Val Glu Ile Lys
            100                 105

<210> SEQ ID NO 13
<211> LENGTH: 121
<212> TYPE: PRT
<213> ORGANISM: Artificial Sequence
<220> FEATURE:
<223> OTHER INFORMATION: Antibody fragment

<400> SEQUENCE: 13

Gln Val Gln Leu Val Gln Ser Gly Ala Glu Leu Val Lys Pro Gly Ala
1               5                   10                  15

Ser Val Lys Leu Ser Cys Lys Ala Ser Gly Tyr Thr Phe Thr Ser His
            20                  25                  30

Trp Met His Trp Val Lys Gln Ala Ala Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Arg Ala Thr Leu Thr Val Asp Lys Ser Thr Ser Thr Ala Tyr
65                  70                  75                  80

Met Gln Leu Ser Ser Leu Thr Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
        115                 120

<210> SEQ ID NO 14
<211> LENGTH: 106
<212> TYPE: PRT
<213> ORGANISM: Artificial Sequence
<220> FEATURE:
<223> OTHER INFORMATION: Antibody fragment

<400> SEQUENCE: 14

Gln Ile Val Leu Thr Gln Ser Pro Ala Thr Leu Ser Ala Ser Pro Gly
1               5                   10                  15

Glu Arg Ala Thr Met Ser Cys Ser Ala Ser Ser Ser Val Thr Tyr Met
            20                  25                  30

Tyr Trp Tyr Gln Gln Lys Pro Gly Gln Ser Pro Arg Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Thr Leu Thr Ile Ser Ser Leu Glu Ala Glu
65                  70                  75                  80

Asp Ala Ala Thr Tyr Tyr Cys Gln Gln Trp Ser Ser His Ile Phe Thr
                85                  90                  95

Phe Gly Gln Gly Thr Lys Val Glu Ile Lys
            100                 105
```

```
<210> SEQ ID NO 15
<211> LENGTH: 121
<212> TYPE: PRT
<213> ORGANISM: Artificial Sequence
<220> FEATURE:
<223> OTHER INFORMATION: Antibody fragment

<400> SEQUENCE: 15

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser His
            20                  25                  30

Trp Met His Trp Val Lys Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Arg Val Thr Ile Thr Val Asp Lys Ser Ser Thr Ala Tyr
65                  70                  75                  80

Met Gln Leu Ser Ser Leu Thr Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
        115                 120

<210> SEQ ID NO 16
<211> LENGTH: 106
<212> TYPE: PRT
<213> ORGANISM: Artificial Sequence
<220> FEATURE:
<223> OTHER INFORMATION: Antibody fragment

<400> SEQUENCE: 16

Gln Ile Val Leu Thr Gln Ser Pro Ala Thr Leu Ser Ala Ser Pro Gly
1               5                   10                  15

Glu Lys Ala Thr Met Thr Cys Ser Ala Ser Ser Ser Val Thr Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Leu Glu Ala Glu
65                  70                  75                  80

Asp Ala Ala Thr Tyr Tyr Cys Gln Gln Trp Ser Ser His Ile Phe Thr
                85                  90                  95

Phe Gly Gln Gly Thr Lys Val Glu Ile Lys
            100                 105
```

US 7,132,511 B2

MODIFIED ANTI-EGFR ANTIBODIES WITH REDUCED IMMUNOGENICITY

This application is the National Stage of International Application No. PCT/EP02/01687, filed on Feb. 18, 2002, which claims priority from European Patent Application No. 01103954.2, filed on Feb. 19, 2001.

FIELD OF THE INVENTION

The present invention relates to antibodies which are directed to the EGF receptor (HER1) to be administered especially to humans and in particular for therapeutic use in tumors. The antibodies are modified antibodies whereby the modification results in a reduced propensity for the antibody to elicit an immune response upon administration to the human subject. The invention in particular relates to the modification of anti-EGFR antibody 425 in its different forms and fragments thereof to result in Mab 425 variants that are substantially non-immunogenic or less immunogenic than any non-modified counterpart when used in vivo. The invention relates furthermore to T-cell epitope peptides derived from said non-modified antibody by means of which it is possible to create modified Mab 425 variants with reduced immunogenicity.

BACKGROUND OF THE INVENTION

The epidermal growth factor receptor (EGF receptor or EGFR), also known as c-erbB1/Her 1, and the product of the neu oncogene (also known as c-erbB2/Her 2) are the members of the EFG receptor super family, which belongs to the large family of receptor tyrosine kinases. They interact at the cell surface with specific growth factors or natural ligands, such as EGF or TGF alpha, thus, activating the receptor tyrosine kinase. A cascade of downstream signaling proteins are activated in general leading to altered gene expression and increased growth rates.

C-erbB2 (Her 2) is a transmembrane tyrosine kinase having a molecular weight of about 185,000 with considerable homology to the EGF receptor (Her 1), although a specific ligand for Her 2 has not yet been clearly identified so far.

The EGF receptor is a transmembrane glycoprotein which has a molecular weight of 170,000 and is found on many epithelial cell types. It is activated by at least three ligands, EGF, TGF-α (transforming growth factor alpha) and amphiregulin. Both epidermal growth factor (EGF) and transforming growth factor-alpha (TGF-α) have been demonstrated to bind to EGF receptor and to lead to cellular proliferation and tumor growth. These growth factors do not bind to Her 2 (Ulrich and Schlesinger, 1990, Cell 61, 203). In contrast to several families of growth factors, which induce receptor dimerization by virtue of their dimeric nature (e.g. PDGF) monomeric growth factors, such as EGF, contain two binding sites for their receptors and, therefore, can cross-link two neighboring EGF receptors (Lemmon et al., 1997, EMBO J. 16, 281). Receptor dimerization is essential for stimulating the intrinsic catalytic activity and for the autophosphorylation of growth factor receptors. It should be remarked that receptor protein tyrosine kinases (PTKs) are able to undergo both homo- and heterodimerization. Clinical studies indicate that both EGF receptor and c-erbB2 are overexpressed in certain types of tumors, especially, breast, ovary, bladder, colon, kidney, head and neck cancers and squamous carcinomas of the lung (Mendelsohn, 1989, Cancer Cells 7, 359; Mendelsohn, 1990, Cancer Biology 1, 339). Therefore, these observations have stimulated preclinical investigations targeting on inhibiting the function of human EGF receptors or c-erbB2 as novel therapeutic approaches to treat cancer (see e.g. Baselga et al., 1996, J. Clin. Oncol. 14, 737; Fan and Mendelsohn, 1998, Curr. Opin. Oncol. 10, 67). It has been reported that, for example, anti-EGF receptor antibodies as well as anti-Her 2 antibodies show fruitful results in human cancer therapy. Thus, humanized monoclonal antibody 4D5 (hMAb 4D5, HERCEPTIN®) is already a commercialized product.

It has been demonstrated that anti-EGF receptor antibodies while blocking EGF and TGF-α binding to the receptor appear to inhibit tumor cell proliferation. In view of these findings, a number of murine and rat monoclonal antibodies against EGF receptor have been developed and tested for their ability inhibit the growth of tumor cells in vitro and in vivo (Modjtahedi and Dean, 1994, J. Oncology 4, 277).

Humanized monoclonal antibody 425 (hMAb 425) (U.S. Pat. No. 5,558,864; EP 0531 472) and chimeric monoclonal antibody 225 (cMAb 225) (Naramura et al., 1993, Cancer Immunol. Immunother. 37, 343–349, WO 96/40210), both directed to the EGF receptor, have shown their efficacy in clinical trials.

The C225 antibody was demonstrated to inhibit EGF-mediated tumor cell growth in vitro and inhibit human tumor formation in vivo in nude mice. The antibody, moreover, appeared to act, above all, in synergy with certain chemotherapeutic agents (i.e., doxorubicin, adriamycin, taxol, and cisplatin) to eradicate human tumors in vivo in xenograft mouse models. Ye et al. (1999, Oncogene 18, 731) have reported that human ovarian cancer cells can be treated successfully with a combination of both cMAb 225 and hMAb 4D5.

There are many instances whereby the efficacy of a therapeutic protein is limited by an unwanted immune reaction to the therapeutic protein. Several mouse monoclonal antibodies have shown promise as therapies in a number of human disease settings but in certain cases have failed due to the induction of significant degrees of a human anti-murine antibody (HAMA) response [Schroff, R. W. et al (1985) Cancer Res. 45: 879–885; Shawler, D. L. et al (1985) J. Immunol. 135: 1530–1535]. For monoclonal antibodies, a number of techniques have been developed in attempt to reduce the HAMA response [WO 89/09622; EP 0239400; EP 0438310; WO 91/06667]. These recombinant DNA approaches have generally reduced the mouse genetic information in the final antibody construct whilst increasing the human genetic information in the final construct. Notwithstanding, the resultant "humanized" antibodies have, in several cases, still elicited an immune response in patients [Issacs J. D. (1990) Sem. Immunol. 2: 449, 456; Rebello, P. R. et al (1999) Transplantation 68: 1417–1420].

Antibodies are not the only class of polypeptide molecule administered as a therapeutic agent against which an immune response may be mounted. Even proteins of human origin and with the same amino acid sequences as occur within humans can still induce an immune response in humans. Notable examples include the therapeutic use of granulocyte-macrophage colony stimulating factor [Wadhwa, M. et al (1999) Clin. Cancer Res. 5: 1353–1361] and interferon alpha 2 [Russo, D. et al (1996) Bri. J. Haem. 94: 300–305; Stein, R. et al (1988) New Engl. J. Med. 318: 1409–1413] amongst others.

A principal factor in the induction of an immune response is the presence within the protein of peptides that can stimulate the activity of T-cells via presentation on MHC class II molecules, so-called "T-cell epitopes". Such potential T-cell epitopes are commonly defined as any amino acid residue sequence with the ability to bind to MHC Class II molecules. Such T-cell epitopes can be measured to establish MHC binding. Implicitly, a "T-cell epitope" means an epitope which when bound to MHC molecules can be recognized by a T-cell receptor (TCR), and which can, at least in principle, cause the activation of these T-cells by engaging a TCR to promote a T-cell response. It is, however, usually understood that certain peptides which are found to bind to MHC Class II molecules may be retained in a protein sequence because such peptides are recognized as "self" within the organism into which the final protein is administered.

It is known, that certain of these T-cell epitope peptides can be released during the degradation of peptides, polypeptides or proteins within cells and subsequently be presented by molecules of the major histocompatability complex (MHC) in order to trigger the activation of T-cells. For peptides presented by MHC Class II, such activation of T-cells can then give rise, for example, to an antibody response by direct stimulation of B-cells to produce such antibodies.

MHC Class II molecules are a group of highly polymorphic proteins which play a central role in helper T-cell selection and activation. The human leukocyte antigen group DR (HLA-DR) are the predominant isotype of this group of proteins and are the major focus of the present invention. However, isotypes HLA-DQ and HLA-DP perform similar functions, hence the present invention is equally applicable to these. The MHC class II DR molecule is made of an alpha and a beta chain which insert at their C-termini through the cell membrane. Each hetero-dimer possesses a ligand binding domain which binds to peptides varying between 9 and 20 amino acids in length, although the binding groove can accommodate a maximum of 11 amino acids. The ligand binding domain is comprised of amino acids 1 to 85 of the alpha chain, and amino acids 1 to 94 of the beta chain. DQ molecules have recently been shown to have an homologous structure and the DP family proteins are also expected to be very similar. In humans approximately 70 different allotypes of the DR isotype are known, for DQ there are 30 different allotypes and for DP 47 different allotypes are known. Each individual bears two to four DR alleles, two DQ and two DP alleles. The structure of a number of DR molecules has been solved and such structures point to an open-ended peptide binding groove with a number of hydrophobic pockets which engage hydrophobic residues (pocket residues) of the peptide [Brown et al *Nature* (1993) 364: 33; Stern et al (1994) *Nature* 368: 215]. Polymorphism identifying the different allotypes of class II molecule contributes to a wide diversity of different binding surfaces for peptides within the peptide binding grove and at the population level ensures maximal flexibility with regard to the ability to recognize foreign proteins and mount an immune response to pathogenic organisms. There is a considerable amount of polymorphism within the ligand binding domain with distinct "families" within different geographical populations and ethnic groups. This polymorphism affects the binding characteristics of the peptide binding domain, thus different "families" of DR molecules will have specificities for peptides with different sequence properties, although there may be some overlap. This specificity determines recognition of Th-cell epitopes (Class II T-cell response) which are ultimately responsible for driving the antibody response to B-cell epitopes present on the same protein from which the Th-cell epitope is derived. Thus, the immune response to a protein in an individual is heavily influenced by T-cell epitope recognition which is a function of the peptide binding specificity of that individual's HLA-DR allotype. Therefore, in order to identify T-cell epitopes within a protein or peptide in the context of a global population, it is desirable to consider the binding properties of as diverse a set of HLA-DR allotypes as possible, thus covering as high a percentage of the world population as possible.

An immune response to a therapeutic protein such as the protein which is object of this invention, proceeds via the MHC class II peptide presentation pathway. Here exogenous proteins are engulfed and processed for presentation in association with MHC class II molecules of the DR, DQ or DP type. MHC Class II molecules are expressed by professional antigen presenting cells (APCs), such as macrophages and dendritic cells amongst others. Engagement of a MHC class II peptide complex by a cognate T-cell receptor on the surface of the T-cell, together with the cross-binding of certain other co-receptors such as the CD4 molecule, can induce an activated state within the T-cell. Activation leads to the release of cytokines further activating other lymphocytes such as B cells to produce antibodies or activating T killer cells as a full cellular immune response. The ability of a peptide to bind a given MHC class II molecule for presentation on the surface of an APC is dependent on a number of factors most notably its primary sequence. This will influence both its propensity for proteolytic cleavage and also its affinity for binding within the peptide binding cleft of the MHC class II molecule. The MHC class II/peptide complex on the APC surface presents a binding face to a particular T-cell receptor (TCR) able to recognize determinants provided both by exposed residues of the peptide and the MHC class II molecule.

In the art there are procedures for identifying synthetic peptides able to bind MHC class II molecules (e.g. WO98/52976 and WO00/34317). Such peptides may not function as T-cell epitopes in all situations, particularly, in vivo due to the processing pathways or other phenomena. T-cell epitope identification is the first step to epitope elimination. The identification and removal of potential T-cell epitopes from proteins has been previously disclosed. In the art methods have been provided to enable the detection of T-cell epitopes usually by computational means scanning for recognized sequence motifs in experimentally determined T-cell epitopes or alternatively using computational techniques to predict MHC class II-binding peptides and in particular DR-binding peptides. WO98/52976 and WO00/34317 teach computational threading approaches to identifying polypeptide sequences with the potential to bind a sub-set of human MHC class II DR allotypes. In these teachings, predicted T-cell epitopes are removed by the use of judicious amino acid substitution within the primary sequence of the therapeutic antibody or non-antibody protein of both non-human and human derivation.

Other techniques exploiting soluble complexes of recombinant MHC molecules in combination with synthetic peptides and able to bind to T-cell clones from peripheral blood samples from human or experimental animal subjects have been used in the art [Kern, F. et al (1998) *Nature Medicine* 4:975–978; Kwok, W. W. et al (2001) *TRENDS in Immunology* 22: 583–588] and may also be exploited in an epitope identification strategy.

As depicted above and as consequence thereof, it would be desirable to identify and to remove or at least to reduce T-cell epitopes from a given in principal therapeutically valuable but originally immunogenic polypeptide, protein or immunoglobulin.

Modified Mab 425 was already provided earlier (U.S. Pat. No. 5,558,864; EP 0531 472) as well as chimeric and humanized versions of c225 (WO 96/40210) but these approaches have been directed towards the reduction of immunogenicity by preparing the chimeric and humanized versions of said antibodies from the murine forms by standard methods. Such teachings do not recognize the importance of T-cell epitopes to the immunogenic properties of the protein nor have been conceived to directly influence said properties in a specific and controlled way according to the scheme of the present invention.

However, there is a continued need for anti-EGFR antibodies with enhanced properties. Desired enhancements include alternative schemes and modalities for the expression and purification of the said therapeutic, but also and especially, improvements in the biological properties of the immunoglobulin. There is a particular need for enhancement of the in vivo characteristics when administered to the human subject. In this regard, it is highly desired to provide anti-EGFR antibodies, especially MAb 425 with reduced or absent potential to induce an immune response in the human subject.

SUMMARY OF THE INVENTION

The present invention provides for modified forms of anti-EGFR antibodies, preferably MAb 425, in which the immune characteristic is modified by means of reduced or removed numbers of potential T-cell epitopes.

The invention discloses sequences identified within the MAb 425 primary sequence that are potential T-cell epitopes by virtue of MHC class II binding potential.

The invention discloses also specific positions within the primary sequence of the molecule which according to the invention are to be altered by specific amino acid substitution, addition or deletion without in principal affecting the biological activity. In cases in which the loss of immunogenicity can be achieved only by a simultaneous loss of biological activity or antibody specificity/avidity it is possible to restore said parameters by further alterations within the amino acid sequence of the antibody variant.

The invention furthermore discloses methods to produce such modified antibodies, and above all methods to identify said T-cell epitopes which require alteration in order to reduce or remove immunogenic sites.

The anti-EGFR antibody modified according to this invention would expect to display an increased circulation time within the human subject and would be of particular benefit in chronic or recurring disease settings such as is the case for a number of indications. The present invention provides for modified forms of said antibody proteins that are expected to display enhanced properties in vivo. These modified anti-EGFR antibody molecules can be used in pharmaceutical compositions.

In summary the invention relates to the following issues:

a modified antibody or fragment thereof directed to the EGF receptor (Her 1) being substantially non-immunogenic or less immunogenic than any original immunogenicly non-modified antibody directed to the same receptor when exposed to the immune system of a given species and compared with the non-modified antibody, wherein the modified antibody comprises—compared with the originally non-modified antibody—no or a reduced number of T-cell epitope sequences and/or MHC allotypes having the ability to bind peptides derived from said non-modified antibody;

an accordingly specified modified antibody, wherein said originally present T-cell epitopes are MHC class II ligands or peptide sequences which show the ability to stimulate or bind T-cells via presentation on class II;

an accordingly specified modified antibody, wherein 1–9 amino acid residues, preferably one amino acid residue, in any of the originally present T-cell epitopes are (is) altered;

an accordingly specified modified antibody, wherein the alteration of the amino acid residues is substitution, deletion or addition of originally present amino acid(s) residue(s) by other amino acid residue(s) at specific position(s);

an accordingly specified modified antibody, wherein additionally further substitution, addition or deletion of specific amino acid(s) is conducted to restore biological activity of said molecule;

an accordingly specified modified antibody, wherein the amino acid alteration is made with reference to an homologous protein sequence and/or with reference to in silico modeling techniques;

an accordingly specified modified antibody, wherein said original immunogenicly non-modified antibody comprises sequences deriving completely or partially from non-human origin;

an accordingly specified modified antibody, wherein said original immunogenicly non-modified antibody is a chimeric antibody or a non-human antibody comprising surface residues except those being not close to the CDR regions, which derive from corresponding human reference framework sequences (veneered antibody);

an accordingly specified modified antibody, wherein said original immunogenicly non-modified antibody is murine MAb 425, preferably comprising any of the sequences as depicted in Table 5;

a DNA sequence coding for the heavy and/or light chain of a modified antibody as specified above;

a pharmaceutical composition comprising a modified anti-EGFR antibody as defined above, optionally together with a pharmaceutically acceptable carrier, diluent or excipient;

a corresponding pharmaceutical composition or kit comprising a further pharmacologically effective drug preferably a cytotoxic agent, more preferably a chemotherapeutic agent;

a method for manufacturing a modified antibody or a fragment thereof directed to the EGF receptor (Her 1) being substantially non-immunogenic or less immunogenic than any original immunogenicly non-modified antibody directed to the same receptor when exposed to the immune system of a given species and compared with the non-modified antibody comprising the following steps: (i) determining the amino acid sequence of the heavy and/or light chain of the original immunogenicly non-modified antibody or part thereof, (ii) identifying one or more potential T-cell epitopes within the amino acid sequence of the antibody by any method including determination of the binding of the peptides to MHC molecules using in vitro or in silico techniques or biological assays, (iii) designing new sequence variants with one or more amino acids within the identified potential T-cell epitopes modified in such a way to substantially reduce or eliminate the activity of the T-cell epitope as determined by the binding of the peptides to MHC molecules using in vitro or in silico techniques or biological assays, or by binding of peptide-MHC complexes to T-cells, (iv) constructing such sequence variants by recombinant DNA techniques and testing said variants in order to identify one or more variants with desirable properties; and (v) optionally repeating steps (ii)–(iv);

the accordingly specified method, wherein step (iii) is carried out by substitution, addition or deletion of 1–9 amino acid residues in any of the originally present T-cell epitopes, optionally with reference to a homologues protein sequence and/or in silico modeling techniques;

an accordingly specified method, wherein step (ii) is carried out by the following steps: (a) selecting a region of the peptide having a known amino acid residue sequence; (b) sequentially sampling overlapping amino acid residue segments of predetermined uniform size and constituted by at least three amino acid residues from the selected region; (c) calculating MHC Class II molecule binding score for each said sampled segment by summing assigned values for each hydrophobic amino acid residue side chain present in said sampled amino acid residue segment; and (d) identifying at least one of said segments suitable for modification, based on the calculated MHC Class II molecule binding score for that segment, to change overall MHC Class II binding score for the peptide without substantially the reducing therapeutic utility of the peptide;

an accordingly specified method, wherein step (c) is carried out by using a Böhm scoring function modified to include 12-6 van der Waal's ligand-protein energy repulsive term and ligand conformational energy term by (1) providing a first data base of MHC Class II molecule models, (2) providing a second data base of allowed peptide backbones for said MHC Class II molecule models, (3) selecting a model from said first data base, (4) selecting an allowed peptide backbone from said second data base, (5) identifying amino acid residue side chains present in each sampled segment, (6) determining the binding affinity value for all side chains present in each sampled segment, and repeating steps (1) through (5) for each said model and each said backbone;

an accordingly specified method, wherein an original immunogenicly non-modified antibody is used which comprises sequences deriving completely or partially from non-human origin;

an accordingly specified method, wherein said original immunogenicly non-modified antibody is a chimeric antibody, or a non-human antibody comprising surface residues except those being not close to the CDR regions, which derive from corresponding human reference framework sequences (veneered antibody);

an accordingly specified method, wherein said original immunogenicly non-modified antibody is a murine antibody, preferably murine MAb 425;

a use of a 13mer T-cell epitope peptide, preferably an at least 9 consecutive amino acid residue peptide of said 13mer T-cell epitope, having a potential MHC class II binding activity and created from an immunogenicly non-modified antibody for the manufacture of an immungenicly modified antibody having substantially no or less immunogenicity when used in vivo compared with said non-modified antibody, each antibody specified above and in the claims.

The general method of the present invention leading to the modified anti-EGFR antibodies according to the invention comprises the following steps:

(a) determining the amino acid sequence of the antibody or part thereof;
(b) identifying one or more potential T-cell epitopes within the amino acid sequence of the immunoglobulin by any method including determination of the binding of the peptides to MHC molecules using in vitro or in silico techniques or biological assays;
(c) designing new sequence variants with one or more amino acids within the identified potential T-cell epitopes modified in such a way to substantially reduce or eliminate the activity of the T-cell epitope as determined by the binding of the peptides to MHC molecules using in vitro or in silico techniques or biological assays. Such sequence variants are created in such a way to avoid creation of new potential T-cell epitopes by the sequence variations unless such new potential T-cell epitopes are, in turn, modified in such a way to substantially reduce or eliminate the activity of the T-cell epitope; and
(d) constructing such sequence variants by recombinant DNA techniques and testing said variants in order to identify one or more variants with desirable properties according to well known recombinant techniques.

The identification of potential T-cell epitopes according to step (b) can be carried out according to methods describes previously in the prior art. Suitable methods are disclosed in WO 98/59244; WO 98/52976; WO 00/34317 and may preferably be used to identify binding propensity of Mab 425-derived peptides to an MHC class II molecule. Another very efficacious method for identifying T-cell epitopes by calculation is described in the EXAMPLE which is a preferred embodiment according to this invention.

In practice a number of variant anti-EGFR immunoglobulins, preferably MAb 425 will be produced and tested for the desired immune and functional characteristic. The variant antibodies will most preferably be produced by recombinant DNA techniques although other procedures including chemical synthesis of antibody fragments may be contemplated.

The invention relates to antibody analogues in which substitutions of at least one amino acid residue have been made at positions resulting in a substantial reduction in activity of or elimination of one or more potential T-cell epitopes from the protein. One or more amino acid substitutions at particular points within any of the potential MHC class II ligands identified in Table 1 may result in a MAb 425 with a reduced immunogenic potential when administered as a therapeutic to the human host. Preferably, amino acid substitutions are made at appropriate points within the peptide sequence predicted to achieve substantial reduction or elimination of the activity of the T-cell epitope. In practice an appropriate point will preferably equate to an amino acid residue binding within one of the pockets provided within the MHC class II binding groove.

It is most preferred to alter binding within the first pocket of the cleft at the so-called P1 or P1 anchor position of the peptide. The quality of binding interaction between the P1 anchor residue of the peptide and the first pocket of the MHC class II binding groove is recognized as being a major determinant of overall binding affinity for the whole peptide. An appropriate substitution at this position of the peptide will be for a residue less readily accommodated within the pocket, for example, substitution to a more hydrophilic residue.

Amino acid residues in the peptide at positions equating to binding within other pocket regions within the MHC binding cleft are also considered and fall under the scope of the present.

It is understood that single amino acid substitutions within a given potential T-cell epitope are the most preferred route by which the epitope may be eliminated. Combinations of substitution within a single epitope may be contemplated and for example can be particularly appropriate where individually defined epitopes are in overlap with each other. Moreover, amino acid substitutions either singly within a given epitope or in combination within a single epitope may be made at positions not equating to the "pocket residues" with respect to the MHC class II binding groove, but at any point within the peptide sequence. Substitutions may be made with reference to an homologues structure or structural method produced using in silico techniques known in the art and may be based on known structural features of the molecule according to this invention. All such substitutions fall within the scope of the present invention.

Amino acid substitutions other than within the peptides identified above may be contemplated particularly when made in combination with substitution(s) made within a listed peptide. For example a change may be contemplated to restore structure or biological activity of the variant molecule. Such compensatory changes and changes to include deletion or addition of particular amino acid residues from the anti-EGFR antibody resulting in a variant with desired activity and in combination with changes in any of the disclosed peptides fall under the scope of the present.

In as far as this invention relates to modified anti-EGFR antibodies, preferably MAb 425, compositions containing such modified immunoglobulins or fragments thereof fusion proteins thereof and related compositions should be considered within the scope of the invention. In another aspect, the present invention relates to nucleic acids encoding modified anti-EGFR antibodies, preferably MAb 425. In a further aspect the present invention relates to methods for therapeutic treatment of humans using the modified immunoglobulins.

DETAILED DESCRIPTION OF THE INVENTION

It should be pointed out, that the term "less or reduced immunogenicity" used before and hereafter is a relative term and relates to the immunogenicity of the respective original source antibody when exposed in vivo to the same species compared with the antibody modified according to the invention. Thus, the source antibody may be a completely non-human antibody, such as a mouse or rat antibody. However, the invention also relates to antibodies which already contain human sequences, such as chimeric or humanized antibodies. In these artificially designed antibodies obtained by classical standard methods there are sequences within the primary structure that are still immunogenic. It is also possible that while creating such chimeric or humanized versions by the well-known methods new T-cell epitopes are generated. Even fully human antibodies or fragments thereof may be immunogenic for certain human individuals or groups of individuals having a genetic immunologically different pattern. The term "chimeric antibody" means antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g.: U.S. Pat. No. 4,816,567; Morrison et al., *Proc. Nat. Acad. Sci*. USA, 81:6851–6855 (1984)). Methods for making chimeric and humanized antibodies are also known in the art. For example, methods for making chimeric antibodies include those described in patents by Boss (Celltech) and by Cabilly (Genentech) (U.S. Pat. No. 4,816,397; U.S. Pat. No. 4,816,567). "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397). "Antibody fragments" comprise a portion of an intact antibody, preferably comprising the antigen-binding or variable region thereof. Examples of antibody fragments include Fab, Fab', F(ab')2, Fv and Fc fragments, diabodies, linear antibodies, single-chain antibody molecules; and multispecific antibodies formed from antibody fragment(s). An "intact" antibody is one which comprises an antigen-binding variable region as well as a light chain constant domain (CL) and heavy chain constant domains, CH1, CH2 and CH3. Preferably, the intact antibody has one or more effector functions. Papain digestion of antibodies produces two identical antigen-binding fragments, called "Fab" fragments, each comprising a single antigen-binding site and a CL and a CH1 region, and a residual "Fc" fragment, whose name reflects its ability to crystallize readily. The "Fc" region of the antibodies comprises, as a rule, a CH2, CH3 and the hinge region of an IgG1 or IgG2 antibody major class. Pepsin treatment yields an "F(ab')2" fragment that has two antigen-binding sites and is still capable of cross-linking antigen. "Fv" is the minimum antibody fragment which contains a complete antigen-recognition and antigen-binding site. This region consists of a dimer of one heavy chain and one light chain variable domain in tight, non-covalent association. "Single-chain Fv" or "scFv" antibody fragments comprise the VH, and VL, domains of antibody, wherein these domains are present in a Single polypeptide chain. Preferably, the Fv polypeptide further comprises a polypeptide linker between the VH and VL domains which enables the scFv to form the desired structure for antigen binding. Single-chain FV antibodies are known, for example, from Plückthun (*The Pharmacology of Monoclonal Antibodies*, Vol. 113, Rosenburg and Moore eds., Springer-Verlag, N.Y., pp. 269–315 (1994)), WO93/16185; U.S. Pat. No. 5,571,894; U.S. Pat. No. 5,587,458; Huston et al. (1988, *Proc. Natl. Acad. Sci*. 85, 5879) or Skerra and Plueckthun (1988, Science 240, 1038).

The term "T-cell epitope" means according to the understanding of this invention an amino acid sequence which is able to bind MHC class II, able to stimulate T-cells and/or also to bind (without necessarily measurably activating) T-cells in complex with MHC class II. The term "peptide" as used herein and in the appended claims, is a compound that includes two or more amino acids. The amino acids are linked together by a peptide bond (defined herein below). There are 20 different naturally occurring amino acids involved in the biological production of peptides, and any number of them may be linked in any order to form a peptide chain or ring. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptides contain only a few amino acid units. Short peptides, e.g., having less than ten amino acid units, are sometimes referred to as "oligopeptides". Other peptides contain a large number of amino acid residues, e.g. up to 100 or more, and are referred to as "polypeptides". By convention, a "polypeptide" may be considered as any peptide chain containing three or more amino acids, whereas a "oligopeptide" is usually considered as a particular type of "short" polypeptide. Thus, as used herein, it is understood that any reference to a "polypeptide" also includes an oligopeptide. Further, any reference to a "peptide" includes polypeptides, oligopeptides, and proteins. Each different arrangement of amino acids forms different polypeptides or proteins. The number of polypeptides—and hence the number of different proteins—that can be formed is practically unlimited. The term "modified protein/antibody" as used according to this invention describes a protein/antibody which has reduced number of T-cell epitopes and elicits therefore a reduced immunogenicity relative to the parent protein when exposed to the immune system of a given species. The term "non-modified protein" as used according to this invention describes the "parent" protein as compared to the "modified protein" and has a larger number of T-cell epitopes and, therefore, an enhanced immunogenicity relative to the modified protein when exposed to the immune system of a given species.

"Alpha carbon (Cα)" is the carbon atom of the carbon-hydrogen (CH) component that is in the peptide chain. A "side chain" is a pendant group to Cα that can comprise a simple or complex group or moiety, having physical dimensions that can vary significantly compared to the dimensions of the peptide.

In the following paragraphs the invention is described in more detail for the monoclonal anti-EGFR antibody 425 which was shown to have a high therapeutic value. However, the invention is not limited to this antibody and its several existing forms, but can be extended to other anti-EGFR antibodies, above all chimeric antibody 225, which has very similar properties.

Unless stated otherwise all amino acids in the variable heavy and light chains are numbered as in Kabat et al, 1991 (Sequences of Proteins of Immunological Interest, US Department of Health and Human Services). Potential T-cell epitopes are numbered with the linear number of the first amino acid of an epitope, counting from the first amino acid of the heavy and light chains.

1. Comparison with Mouse Subgroup Frameworks

The amino acid sequences of murine 425 VH (heavy chain) and VK (light chain) were compared to consensus sequences for the Kabat murine heavy and light chain subgroups. 425 VH can be assigned to mouse heavy chains subgroup IIB. The comparison with the consensus sequence for this subgroup shows that the serine at position 94 in 425 VH is unusual. The most common residue at this position is arginine. 425 VK can be assigned to mouse kappa chains subgroup V1. The comparison with the consensus sequence for this subgroup shows that the residues at positions 45–47, 60 and 100 in 425 VK are unusual for this subgroup. Amino acid residue numbering is as per Kabat.

2. Comparison with Human Frameworks

The amino acid sequences of murine 425 VH (variable heavy chain) and VK (variable kappa light chain) were compared to the sequences of the directory of human germline VH (Tomlinson, I. M. et al., (1992) J. Mol. Biol. 227: 776–798) and VK (Cox, J. P. L. et al., (1994) Eur. J. Immunol. 24:827–836) sequences and also to human germline J region sequences (Routledge, E. G. et al., in, *Protein Engineering of Antibody Molecules for Prophylactic and Therapeutic Applications in Man*, Clark, M. ed. Academic Titles, Nottingham, U K, pp 13–44, 1991). The murine 425 sequence of the heavy and light chain can be taken, for example, from EP 0531 472.

The reference human framework selected for 425 VH was VH1GRR with human JH6. The sequence of VH1GRR in the directory ends at residue 88. Therefore there is no corresponding residue for the unusual serine at position 94 of the murine sequence. This germline sequence has been found in a rearranged mature antibody gene with 4 amino acid changes. The reference human framework selected for 425 VK was L6/vg with human JK2. This germline sequence has been found in a rearranged mature antibody heavy chain with no amino acid changes.

3. Design of "Veneered" Sequences

Following identification of the reference human framework sequences, certain non-identical amino acid residues within the 425 VH and VK frameworks were changed to the corresponding amino acid in the human reference framework sequence. Residues which are considered to be critical for antibody structure and binding were excluded from this process and not altered. The murine residues that were retained at this stage are largely non-surface, buried residues, apart from residues at the N-terminus for instance, which are close to the CDRs in the final antibody (1–8, preferably 1–5 amino acid residues). This process produces a sequence that is broadly similar to a "veneered" antibody as the surface residues are mainly human and the buried residues are as in the original murine sequence.

4. Peptide Threading Analysis

The murine and veneered 425 VH and VK sequences were analyzed using the method according of the invention. The amino acid sequences are divided into all possible 13mers. The 13mer peptides are sequentially presented to the models of the binding groove of the HLA-DR allotypes and a binding score assigned to each peptide for each allele. A conformational score is calculated for each pocket-bound side chain of the peptide. This score is based on steric overlap, potential hydrogen bonds between peptide and residues in the binding groove, electrostatic interactions and favorable contacts between peptide and pocket residues. The conformation of each side chain is then altered and the score recalculated. Having determined the highest conformational score, the binding score is then calculated based on the groove-bound hydrophobic residues, the non-groove hydrophilic residues and the number of residues that fit into the binding groove. Peptides which are known binders to human MHC Class II achieve a high binding score with almost no false negatives. Thus peptides that achieve a significant binding score in the current analysis are considered to be potential T-cell epitopes. The results of the peptide threading analysis are shown in Table 1 for 425 VH and 425 VK. Potential T Cell epitopes are referred to by the linear number of the first residue of the 13mer.

TABLE 1

Potential T cell epitopes in murine and veneered 425 sequences

| Sequence | Number of potential T cell epitopes | Number of first residue of 13 mer with number of bonding alleles in brackets |
|---|---|---|
| Murine 425 VH | 8 | 31(7), 35(17), 43(7), 46(8), 58(10), 62(12), 81(11), 84(16) |
| Veneered 425 VH | 7 | 31(7), 43(7), 46(8), 58(10), 62(11), 81(11), 84(16) |
| Murine 425 VK | 9 | 1(8), 2(5), 17(5), 27(5), 43(16), 72(18), 75(10), 92(10), 93(17) |
| Veneered 425 VK | 4 | 27(5), 43(16), 92(8), 93(17) |

5. Removal of Potential T Cell Epitopes

The numbering of amino acid residues for substitution is as per Kabat. Potential T Cell epitopes are referred to by the linear number of the first residue of the 13mer.

The amino acid substitutions required to remove the potential T cell epitopes from the veneered 425 heavy chain variable region were as follows:

Substitution of proline for alanine at residue 41 (Kabat number 41) removes the potential epitope at residue number 31.

Substitution of proline for leucine at residue 45 (Kabat number 45) removes the potential epitope at residue number 43. A proline at position 45 is found in a human germline VH sequence, DP52.

Substitution of alanine for isoleucine at residue 48 (Kabat number 48) removes the potential epitope at residue number 46.

Substitution of valine for alanine at residue 68 (Kabat number 67) removes the potential epitope at residue number 58.

Substitution of isoleucine for leucine at residue 70 (Kabat number 69) removes the potential epitope at residue number 62.

Substitution of threonine for serine at residue 91 (Kabat number 87) removes the potential epitopes at residue numbers 81 and 84.

The amino acid substitutions required to remove the potential T cell epitopes from the veneered 425 light chain variable region were as follows:

Substitution of histidine for tyrosine at residue 35 (Kabat number 36) removes the potential epitope at residue number 27

Substitution of alanine for threonine at residue 50 (Kabat number 51) removes the potential epitope at residue number 43. This residue is within CDR2. Alanine is commonly found at this position in both human and murine antibodies. An alternative substitution to eliminate this epitope is alanine for leucine at position 45 (Kabat number 46). There is no conservative substitution that will eliminate the potential epitope. Alanine is found at this position in some antibodies.

Substitution of proline for isoleucine at residue 94 (Kabat number 95) removes the potential epitope at residue number 92. Kabat residue 95 is within CDRL3. Proline is common at this position in mouse antibody sequences and there is no change outwith the CDR that eliminates the potential epitope.

Substitution of valine for leucine at residue 103 (Kabat number 104) removes the potential epitope at residue number 93.

6. Design of De-immunized Sequences

De-immunized heavy and light chain variable region sequences were designed with reference to the changes required to remove potential T cell epitopes and consideration of framework residues that might be critical for antibody structure and binding. In addition to the De-immunized sequences based on the veneered sequence an additional sequence was designed for each of VH and VK based on the murine sequence, termed the Mouse Peptide Threaded (Mo PT) version. For this version, changes were made directly to the murine sequence in order to eliminate T cell epitopes, but only changes out with the CDRs that are not considered to be detrimental to binding are made. No attempt to remove surface (B-cell) epitopes has been made in this version of the de-immunized sequence.

The primary de-immunized VH includes substitutions 1 to 6 in Section 5 above and includes no potential T cell epitopes. A further 4 de-immunized VH sequences were designed in order to test the effect of the various substitutions required on antibody binding. The cumulative alterations made to the primary de-immunized sequence (425 VH1GRR-VH-v1) and the potential T cell epitopes remaining are detailed in Table 2. The mouse threaded version is included for comparison.

TABLE 2

Amino acid changes and potential epitopes in de-immunized 425 VH

| Variant | Cumulative Residue Changes | Potential T Cell Epitopes |
|---|---|---|
| 425 VH1GRR-VH-v1 | None | None |
| 425 VH1GRR-VH-v2 | 48A → I | 46(8) |
| 425 VH1GRR-VH-v3 | 45P → L | 43(7), 46(8) |
| 425 VH1GRR-VH-v4 | 67V → A, 69I → L | 43(7), 46(8), 58(10), 62(11) |
| 425 VH1GRR-VH-v5 | 41P → A | 31(7), 43(7), 46(8), 58(10), 62(11) |
| 425 VH-MoPT | NA | 43(7), 46(8) |

The primary de-immunized VK includes substitutions 1 to 4 in Section 5 above and includes no potential T cell epitopes. A further 4 de-immunized VK sequences were designed in order to test the effect of the various substitutions required on antibody binding. Version 2 is an alternative to Version 1 in which an alternative substitution has been used to remove the same potential T-cell epitope. The cumulative alterations made to the primary de-immunized sequence (425 L6-vg-VK-v1) and the potential T cell epitopes remaining are detailed in Table 3. The mouse threaded version is included for comparison.

TABLE 3

Amino acid changes and potential epitopes in de-immunized 425 VK

| Variant | Cumulative Residue Changes | Potential T cell Epitopes |
|---|---|---|
| 425 L6-vg-VK-v1 | None | None |
| 425 L6-vg-VK-v1 | 51 A → T, 46L → A | None |
| 425 L6-vg-VK-v1 | 46 A → L | 43(16) |
| 425 L6-vg-VK-v1 | 95 P → I | 43(16), 92(8) |
| 425 L6-vg-VK-v1 | 36 H → Y | 27(5), 43(16), 92(8) |
| 425 VK-MoPT | NA | 27(5), 43(16), 92(8) |

TABLE 4 original and "veneered" sequences of VH and VK of murine MAb 425

425 VH mouse
QVQLQQPGAELVKPGASVKLSCKASGYTFTSHWMHWVKQRAGQGLEWIGEFNPSNGRTNYNEKFK
SKATLTVDKSSSTAYMQLSSLTSEDSAVYYCASRDYDYDGRYFDYWGQGTTLTVSS
(SEQ ID NO: 1);
425 VK mouse
QIVLTQSPAIMSASPGEKVTMTCSASSSVTYMYWYQQKPGSSPRLLIYDTSNLASGVPVRFSGSG
SGTSYSLTISRMEAEDAATYYCQQWSSHIFTFGSGTKLEIK
(SEQ ID NO: 2);
425 VH veneered:
QVQLVQSGAELVKPGASVKLSCKASGYTFTSHWMHWVKQAAGQGLEWIGEFNPSNGRTNYNEKFK
SRATLTVDKSTSTAYMQLSSLTSEDSAVYYCASRDYDYDGRYFDYWGQGTTLTVSS
(SEQ ID NO: 3);
425 VK veneered:
QIVLTQSPATLSASPGERATMSCSASSSVTYMYWYQQKPGQSPRLLIYDTSNLASGVPARFSGSG
SGTSYTLTISSLEAEDAATYYCQQWSSHIFTFGQGTKLEIK
(SEQ ID NO: 4)

TABLE 5

De-immunized sequences of variable heavy and light chain of MAb 425

425 de-immunized VH1
QVQLVQSGAELVKPGASVKLSCKASGYTFTSHWMHWVKQAPGQGPEWAGEFNPSNGRTNYNEKFK
SRVTITVDKSTSTAYMQLSSLTSEDTAVYYCASRDYDYDGRYFDYWGQGTTLTVSS
(SEQ ID NO: 5);
425 de-immunized VK1
QIVLTQSPATLSASPGERATMSCSASSSVTYMYWHQQKPGQSPRLLIYDASNLASGVPARFSGSG
SGTSYTLTISSLEAEDAATYYCQQWSSHPFTFGQGTKVEIK
(SEQ ID NO: 6);
425 de-immunized VH2
QVQLVQSGAELVKPGASVKLSCKASGYTFTSHWMHWVKQAPGQGPEWIGEFNPSNGRTNYNEKFK
SRVTITVDKSTSTAYMQLSSLTSEDTAVYYCASRDYDYDGRYFDYWGQGTTLTVSS
(SEQ ID NO: 7);
425 de-immunized VK2
QIVLTQSPATLSASPGERATMSCSASSSVTYMYWHQQKPGQSPRALIYDTSNLASGVPARFSGSG
SGTSYTLTISSLEAEDAATYYCQQWSSHPFTFGQGTKVEIK
(SEQ ID NO: 8);
425 de-immunized VH3
QVQLVQSGAELVKPGASVKLSCKASGYTFTSHWMHWVKQAPGQGLEWIGEFNPSNGRTNYNEKFK
SRVTITVDKSTSTAYMQLSSLTSEDTAVYYCASRDYDYDGRYFDYWGQGTTLTVSS
(SEQ ID NO: 9);
425 de-immunized VK3
QIVLTQSPATLSASPGERATMSCSASSSVTYMYWHQQKPGQSPRLLIYDTSNLASGVPARFSGSG
SGTSYTLTISSLEAEDAATYYCQQWSSHPFTFGQGTKVEIK
(SEQ ID NO: 10);
425 de-immunized VH4
QVQLVQSGAELVKPGASVKLSCKASGYTFTSHWMHWVKQAPGQGLEWIGEFNPSNGRTNYNEKFK
SRATLTVDKSTSTAYMQLSSLTSEDTAVYYCASRDYDYDGRYFDYWGQGTTLTVSS
(SEQ ID NO: 11);
425 de-immunized VK4
QIVLTQSPATLSASPGERATMSCSASSSVTYMYWHQQKPGQSPRLLIYDTSNLASGVPARFSGSG
SGTSYTLTISSLEAEDAATYYCQQWSSHIFTFGQGTKVEIK
(SEQ ID NO: 12);
425 de-immunized VH5
QVQLVQSGAELVKPGASVKLSCKASGYTFTSHWMHWVKQAAGQGLEWIGEFNPSNGRTNYNEKFK
SRATLTVDKSTSTAYMQLSSLTSEDTAVYYCASRDYDYDGRYFDYWGQGTTLTVSS
(SEQ ID NO: 13);
425 de-immunized VK5
QIVLTQSPATLSASPGERATMSCSASSSVTYMYWYQQKPGQSPRLLIYDTSNLASGVPARFSGSG
SGTSYTLTISSLEAEDAATYYCQQWSSHIFTFGQGTKVEIK
(SEQ ID NO: 14);
425 VH mouse, peptide threaded (Mo PT)
QVQLQQPGAELVKPGASVKLSCKASGYTFTSHWMHWVKQAPGQGLEWIGEFNPSNGRTNYNEKFK
SRVTITVDKSSSTAYMQLSSLTSEDTAVYYCASRDYDYDGRYFDYWGQGTTLTVSS
(SEQ ID NO: 15);
425 VK mouse, peptide threaded (Mo PT)
QIVLTQSPATLSASPGEKATMTCSASSSVTYMYWYQQKPGSSPRLLIYDTSNLASGVPVRFSGSG
SGTSYSLTISRLEAEDAATYYCQQWSSHIFTFGQGTKVEIK
(SEQ ID NO: 16)

As already mentioned, the modified anti-EGFR antibodies according to the invention, preferably MAb 425, can be used in pharmaceutical compositions and pharmaceutical kits preferably for the treatment of cancer. "Cancer" and "tumor" refer to or describe the physiological condition in mammals that is typically characterized by unregulated cell growth. By means of the pharmaceutical compositions according of the present invention tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver.

The pharmaceutical compositions of the invention can comprise agents that reduce or avoid side effects associated with the combination therapy of the present invention ("adjunctive therapy"), including, but not limited to, those agents, for example, that reduce the toxic effect of anticancer drugs, e.g., bone resorption inhibitors, cardioprotective agents. Said adjunctive agents prevent or reduce the incidence of nausea and vomiting associated with chemotherapy, radiotherapy or operation, or reduce the incidence of infection associated with the administration of myelosuppressive anticancer drugs. Adjunctive agents are well known in the art. The modified antibodies according to the invention can additionally administered with adjuvants such as BCG and other immune system stimulators. Furthermore, the compositions may include chemotherapeutic agents as described above, which contain cytotoxic effective radio labeled isotopes, or other cytotoxic agents, such as a cytotoxic peptides (e.g. cytokines) or cytotoxic drugs and the like. The pharmaceutical kits for treating tumors or tumor metastases refer to a package and, as a rule, instructions for using the reagents in methods to treat tumors and tumor metastases. A reagent in a kit of this invention is typically formulated as a therapeutic composition as described herein, and therefore can be in any of a variety of forms suitable for distribution in a kit. Such forms can include a liquid, powder, tablet, suspension and the like formulation for providing the antagonist and/or the fusion protein of the present invention. The reagents may be provided in separate containers suitable for administration separately according to the present methods, or alternatively may be provided combined in a composition in a single container in the package. The package may contain an amount sufficient for one or more dosages of reagents according to the treatment methods described herein. A kit of this invention also contains "instruction for use" of the materials contained in the package. Pharmaceutically acceptable carriers, diluents and excipients and granunatical variations thereof are materials that are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically, such compositions are prepared as injectables either as liquid solutions or suspensions, however, solid forms suitable for solution, or suspensions, in liquid prior to use can also be prepared. The preparation can also be emulsified. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein.

Typically, a therapeutically effective amount of an anti-EGFR antibody is an amount such that when administered in physiologically tolerable composition is sufficient to achieve a plasma concentration of from about 0.01 microgram (µg) per milliliter (ml) to about 100 µg/ml, preferably from about 1 µg/ml to about 5 µg/ml and usually about 5 µg/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily for one or several days. As a rule, lower dosages as indicated above can be applied with the same efficacy if the immunogenicly modified antibodies according to the invention are used instead of the corresponding non-modified versions.

In cases where combination therapy, for example with chemotherapeutic agents are necessary or recommended, the typical dosage of such an active agent is 10 mg to 1000 mg, preferably about 20 to 200 mg, and more preferably 50 to 100 mg per kilogram body weight per day.

The following example describes in a general form a method for identification T-cell epitopes present on the original antibodies with non-modified immunogenic potential according to the invention. Identification of said epitope sequences can, however, be carried out by the known methods as specified above.

EXAMPLE

There are a number of factors that play important roles in determining the total structure of a protein, polypeptide or immunoglobulin. First, the peptide bond, i.e., that bond which joins the amino acids in the chain together, is a covalent bond. This bond is planar in structure, essentially a substituted amide. An "amide" is any of a group of organic compounds containing the grouping —CONH—.

The planar peptide bond linking Cα of adjacent amino acids may be represented as depicted below:

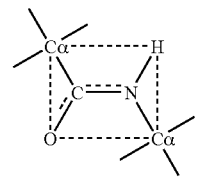

Because the O=C and the C—N atoms lie in a relatively rigid plane, free rotation does not occur about these axes. Hence, a plane schematically depicted by the interrupted line is sometimes referred to as an "amide" or "peptide plane" plane wherein lie the oxygen (O), carbon (C), nitrogen (N), and hydrogen (H) atoms of the peptide backbone. At opposite corners of this amide plane are located the Cα atoms. Since there is substantially no rotation about the O=C and C—N atoms in the peptide or amide plane, a polypeptide chain thus comprises a series of planar peptide linkages joining the Cα atoms.

A second factor that plays an important role in defining the total structure or conformation of a polypeptide or protein is the angle of rotation of each amide plane about the common Cα linkage. The terms "angle of rotation" and "torsion angle" are hereinafter regarded as equivalent terms.

Assuming that the O, C, N, and H atoms remain in the amide plane (which is usually a valid assumption, although there may be some slight deviations from planarity of these atoms for some conformations), these angles of rotation define the N and R polypeptide's backbone conformation, i.e., the structure as it exists between adjacent residues. These two angles are known as $\phi$ and $\psi$. A set of the angles $\phi_1$, $\psi_1$, where the subscript i represents a particular residue of a polypeptide chain, thus effectively defines the polypeptide secondary structure. The conventions used in defining the $\phi$, $\psi$ angles, i.e., the reference points at which the amide planes form a zero degree angle, and the definition of which angle is $\phi$, and which angle is $\psi$, for a given polypeptide, are defined in the literature. See, e.g, Ramachandran et al. *Adv. Prot. Chem.* 23:283–437 (1968), at pages 285–94, which pages are incorporated herein by reference.

The present method can be applied to any protein, and is based in part upon the discovery that in humans the primary Pocket 1 anchor position of MHC Class II molecule binding grooves has a well designed specificity for particular amino acid side chains. The specificity of this pocket is determined by the identity of the amino acid at position 86 of the beta chain of the MHC Class II molecule. This site is located at the bottom of Pocket 1 and determines the size of the side chain that can be accommodated by this pocket. Marshall, K. W., *J. Immunol.*, 152:4946–4956 (1994). If this residue is a glycine, then all hydrophobic aliphatic and aromatic amino acids (hydrophobic aliphatics being: valine, leucine, isoleucine, methionine and aromatics being: phenylalanine, tyrosine and tryptophan) can be accommodated in the pocket, a preference being for the aromatic side chains. If this pocket residue is a valine, then the side chain of this amino acid protrudes into the pocket and restricts the size of peptide side chains that can be accommodated such that only hydrophobic aliphatic side chains can be accommodated. Therefore, in an amino acid residue sequence, wherever an amino acid with a hydrophobic aliphatic or aromatic side chain is found, there is the potential for a MHC Class II restricted T-cell epitope to be present. If the side-chain is hydrophobic aliphatic, however, it is approximately twice as likely to be associated with a T-cell epitope than an aromatic side chain (assuming an approximately even distribution of Pocket 1 types throughout the global population).

A computational method embodying the present invention profiles the likelihood of peptide regions to contain T-cell epitopes as follows:

(1) The primary sequence of a peptide segment of predetermined length is scanned, and all hydrophobic aliphatic and aromatic side chains present are identified. (2) The hydrophobic aliphatic side chains are assigned a value greater than that for the aromatic side chains; preferably about twice the value assigned to the aromatic side chains, e.g., a value of 2 for a hydrophobic aliphatic side chain and a value of 1 for an aromatic side chain. (3) The values determined to be present are summed for each overlapping amino acid residue segment (window) of predetermined uniform length within the peptide, and the total value for a particular segment (window) is assigned to a single amino acid residue at an intermediate position of the segment (window), preferably to a residue at about the midpoint of the sampled segment (window). This procedure is repeated for each sampled overlapping amino acid residue segment (window). Thus, each amino acid residue of the peptide is assigned a value that relates to the likelihood of a T-cell epitope being present in that particular segment (window). (4) The values calculated and assigned as described in Step 3, above, can be plotted against the amino acid coordinates of the entire amino acid residue sequence being assessed. (5) All portions of the sequence which have a score of a predetermined value, e.g., a value of 1, are deemed likely to contain a T-cell epitope and can be modified, if desired.

This particular aspect of the present invention provides a general method by which the regions of peptides likely to contain T-cell epitopes can be described. Modifications to the peptide in these regions have the potential to modify the MHC Class II binding characteristics.

According to another aspect of the present invention, T-cell epitopes can be predicted with greater accuracy by the use of a more sophisticated computational method which takes into account the interactions of peptides with models of MHC Class II alleles. The computational prediction of T-cell epitopes present within a peptide according to this particular aspect contemplates the construction of models of at least 42 MHC Class II alleles based upon the structures of all known MHC Class II molecules and a method for the use of these models in the computational identification of T-cell epitopes, the construction of libraries of peptide backbones for each model in order to allow for the known variability in relative peptide backbone alpha carbon (Cα) positions, the construction of libraries of amino-acid side chain conformations for each backbone dock with each model for each of the 20 amino-acid alternatives at positions critical for the interaction between peptide and MHC Class II molecule, and the use of these libraries of backbones and side-chain conformations in conjunction with a scoring function to select the optimum backbone and side-chain conformation for a particular peptide docked with a particular MHC Class II molecule and the derivation of a binding score from this interaction.

Models of MHC Class II molecules can be derived via homology modeling from a number of similar structures found in the Brookhaven Protein Data Bank ("PDB"). These may be made by the use of semi-automatic homology modeling software (Modeller, Sali A. & Blundell T L., 1993. *J. Mol Biol* 234:779–815) which incorporates a simulated annealing function, in conjunction with the CHARMm force-field for energy minimisation (available from Molecular Simulations Inc., San Diego, Calif.). Alternative modeling methods can be utilized as well.

The present method differs significantly from other computational methods which use libraries of experimentally derived binding data of each amino-acid alternative at each position in the binding groove for a small set of MHC Class II molecules (Marshall, K. W., et al., *Biomed. Pept. Proteins Nucleic Acids,* 1(3):157–162) (1995) or yet other computational methods which use similar experimental binding data in order to define the binding characteristics of particular types of binding pockets within the groove, again using a relatively small subset of MHC Class II molecules, and then 'mixing and matching' pocket types from this pocket library to artificially create further 'virtual' MHC Class II molecules (Stumiolo T., et al., *Nat. Biotech,* 17(6): 555–561 (1999). Both prior methods suffer the major disadvantage that, due to the complexity of the assays and the need to synthesize large numbers of peptide variants, only a small number of MHC Class II molecules can be experimentally scanned. Therefore the first prior method can only make predictions for a small number of MHC Class II molecules. The second prior method also makes the assumption that a pocket lined with similar amino-acids in one molecule will have the same binding characteristics when in the context of a different Class II allele and suffers further disadvantages in that only those MHC Class II molecules can be 'virtually' created which contain pockets contained within the pocket library.

Using the modeling approach described herein, the structure of any number and type of MHC Class II molecules can be deduced, therefore alleles can be specifically selected to be representative of the global population. In addition, the number of SMC Class II molecules scanned can be increased by making further models further than having to generate additional data via complex experimentation.

The use of a backbone library allows for variation in the positions of the C$\alpha$ atoms of the various peptides being scanned when docked with particular MHC Class II molecules. This is again in contrast to the alternative prior computational methods described above which rely on the use of simplified peptide backbones for scanning amino-acid binding in particular pockets. These simplified backbones are not likely to be representative of backbone conformations found in 'real' peptides leading to inaccuracies in prediction of peptide binding. The present backbone library is created by superposing the backbones of all peptides bound to MHC Class II molecules found within the Protein Data Bank and noting the root mean square (RMS) deviation between the C$\alpha$ atoms of each of the eleven amino-acids located within the binding groove. While this library can be derived from a small number of suitable available mouse and human structures (currently 13), in order to allow for the possibility of even greater variability, the RMS figure for each C"-$\alpha$ position is increased by 50%. The average C$\alpha$ position of each amino-acid is then determined and a sphere drawn around this point whose radius equals the RMS deviation at that position plus 50%. This sphere represents all allowed C$\alpha$ positions.

Working from the C$\alpha$ with the least RMS deviation (that of the amino-acid in Pocket 1 as mentioned above, equivalent to Position 2 of the 11 residues in the binding groove), the sphere is three-dimensionally gridded, and each vertex within the grid is then used as a possible location for a C$\alpha$ of that amino-acid. The subsequent amide plane, corresponding to the peptide bond to the subsequent amino-acid is grafted onto each of these C$\alpha$s and the $\phi$ and $\psi$ angles are rotated step-wise at set intervals in order to position the subsequent C$\alpha$. If the subsequent C$\alpha$ falls within the 'sphere of allowed positions' for this C$\alpha$ than the orientation of the dipeptide is accepted, whereas if it falls outside the sphere then the dipeptide is rejected. This process is then repeated for each of the subsequent C$\alpha$ positions, such that the peptide grows from the Pocket 1 C$\alpha$ 'seed', until all nine subsequent C$\alpha$s have been positioned from all possible permutations of the preceding C$\alpha$s. The process is then repeated once more for the single C$\alpha$ preceding pocket 1 to create a library of backbone C$\alpha$ positions located within the binding groove.

The number of backbones generated is dependent upon several factors: The size of the 'spheres of allowed positions'; the fineness of the gridding of the 'primary sphere' at the Pocket 1 position; the fineness of the step-wise rotation of the $\phi$ and $\psi$ angles used to position subsequent C$\alpha$s. Using this process, a large library of backbones can be created. The larger the backbone library, the more likely it will be that the optimum fit will be found for a particular peptide within the binding groove of an MHC Class II molecule. Inasmuch as all backbones will not be suitable for docking with all the models of MHC Class II molecules due to clashes with amino-acids of the binding domains, for each allele a subset of the library is created comprising backbones which can be accommodated by that allele. The use of the backbone library, in conjunction with the models of MHC Class II molecules creates an exhaustive database consisting of allowed side chain conformations for each amino-acid in each position of the binding groove for each MHC Class II molecule docked with each allowed backbone. This data set is generated using a simple steric overlap function where a MHC Class II molecule is docked with a backbone and an amino-acid side chain is grafted onto the backbone at the desired position. Each of the rotatable bonds of the side chain is rotated step-wise at set intervals and the resultant positions of the atoms dependent upon that bond noted. The interaction of the atom with atoms of side-chains of the binding groove is noted and positions are either accepted or rejected according to the following criteria: The sum total of the overlap of all atoms so far positioned must not exceed a pre-determined value. Thus the stringency of the conformational search is a function of the interval used in the step-wise rotation of the bond and the pre-determined limit for the total overlap. This latter value can be small if it is known that a particular pocket is rigid, however the stringency can be relaxed if the positions of pocket side-chains are known to be relatively flexible. Thus allowances can be made to imitate variations in flexibility within pockets of the binding groove. This conformational search is then repeated for every amino-acid at every position of each backbone when docked with each of the MHC Class II molecules to create the exhaustive database of side-chain conformations.

A suitable mathematical expression is used to estimate the energy of binding between models of MHC Class II molecules in conjunction with peptide ligand conformations which have to be empirically derived by scanning the large database of backbone/side-chain conformations described above. Thus a protein is scanned for potential T-cell epitopes by subjecting each possible peptide of length varying between 9 and 20 amino-acids (although the length is kept constant for each scan) to the following computations: An MHC Class II molecule is selected together with a peptide backbone allowed for that molecule and the side-chains corresponding to the desired peptide sequence are grafted on. Atom identity and interatomic distance data relating to a particular side-chain at a particular position on the backbone are collected for each allowed conformation of that amino-acid (obtained from the database described above). This is repeated for each side-chain along the backbone and peptide scores derived using a scoring function. The best score for that backbone is retained and the process repeated for each allowed backbone for the selected model. The scores from all allowed backbones are compared and the highest score is deemed to be the peptide score for the desired peptide in that MHC Class II model. This process is then repeated for each model with every possible peptide derived from the protein being scanned, and the scores for peptides versus models are displayed.

In the context of the present invention, each ligand presented for the binding affinity calculation is an amino-acid segment selected from a peptide or protein as discussed above. Thus, the ligand is a selected stretch of amino acids about 9 to 20 amino acids in length derived from a peptide, polypeptide or protein of known sequence. The terms "amino acids" and "residues" are hereinafter regarded as equivalent terms. The ligand, in the form of the consecutive amino acids of the peptide to be examined grafted onto a backbone from the backbone library, is positioned in the binding cleft of an MHC Class II molecule from the MHC Class II molecule model library via the coordinates of the C"-$\alpha$ atoms of the peptide backbone and an allowed conformation for each side-chain is selected from the database of allowed conformations. The relevant atom identities and interatomic distances are also retrieved from this database and used to calculate the peptide binding score. Ligands with a high binding affinity for the MHC Class II binding pocket are flagged as candidates for site-directed mutagenesis. Amino-acid substitutions are made in the flagged ligand (and hence in the protein of interest) which is then retested using the scoring function in order to determine changes which reduce the binding affinity below a predetermined threshold value. These changes can then be incorporated into the protein of interest to remove T-cell epitopes.

Binding between the peptide ligand and the binding groove of MHC Class II molecules involves non-covalent interactions including, but not limited to: hydrogen bonds, electrostatic interactions, hydrophobic (lipophilic) interactions and Van der Walls interactions. These are included in the peptide scoring function as described in detail below. It should be understood that a hydrogen bond is a non-covalent bond which can be formed between polar or charged groups and consists of a hydrogen atom shared by two other atoms. The hydrogen of the hydrogen donor has a positive charge where the hydrogen acceptor has a partial negative charge. For the purposes of peptide/protein interactions, hydrogen bond donors may be either nitrogens with hydrogen attached or hydrogens attached to oxygen or nitrogen. Hydrogen bond acceptor atoms may be oxygens not attached to hydrogen, nitrogens with no hydrogens attached and one or two connections, or sulphurs with only one connection. Certain atoms, such as oxygens attached to hydrogens or imine nitrogens (e.g. C═NH) may be both hydrogen acceptors or donors. Hydrogen bond energies range from 3 to 7 Kcal/mol and are much stronger than Van der Waal's bonds, but weaker than covalent bonds. Hydrogen bonds are also highly directional and are at their strongest when the donor atom, hydrogen atom and acceptor atom are co-linear. Electrostatic bonds are formed between oppositely charged ion pairs and the strength of the interaction is inversely proportional to the square of the distance between the atoms according to Coulomb's law. The optimal distance between ion pairs is about 2.8 Å. In protein/peptide interactions, electrostatic bonds may be formed between arginine, histidine or lysine and aspartate or glutamate. The strength of the bond will depend upon the pKa of the ionizing group and the dielectric constant of the medium although they are approximately similar in strength to hydrogen bonds.

Lipophilic interactions are favorable hydrophobic-hydrophobic contacts that occur between he protein and peptide ligand. Usually, these will occur between hydrophobic amino acid side chains of the peptide buried within the pockets of the binding groove such that they are not exposed to solvent. Exposure of the hydrophobic residues to solvent is highly unfavorable since the surrounding solvent molecules are forced to hydrogen bond with each other forming cage-like clathrate structures. The resultant decrease in entropy is highly unfavorable. Lipophilic atoms may be sulphurs which are neither polar nor hydrogen acceptors and carbon atoms which are not polar.

Van der Waal's bonds are non-specific forces found between atoms which are 3–4 Å apart. They are weaker and less specific than hydrogen and electrostatic bonds. The distribution of electronic charge around an atom changes with time and, at any instant, the charge distribution is not symmetric. This transient asymmetry in electronic charge induces a similar asymmetry in neighboring atoms. The resultant attractive forces between atoms reaches a maximum at the Van der Waal's contact distance but diminishes very rapidly at about 1 Å to about 2 Å. Conversely, as atoms become separated by less than the contact distance, increasingly strong repulsive forces become dominant as the outer electron clouds of the atoms overlap. Although the attractive forces are relatively weak compared to electrostatic and hydrogen bonds (about 0.6 Kcal/mol), the repulsive forces in particular may be very important in determining whether a peptide ligand may bind successfully to a protein.

In one embodiment, the Böhm scoring function (SCORE1 approach) is used to estimate the binding constant. (Böhm, H. J., *J. Comput Aided Mol. Des.,* 8(3):243–256 (1994) which is hereby incorporated in its entirety). In another embodiment, the scoring function (SCORE2 approach) is used to estimate the binding affinities as an indicator of a ligand containing a T-cell epitope (Böhm, H. J., *J. Comput Aided Mol. Des.,* 12(4):309–323 (1998) which is hereby incorporated in its entirety). However, the Böhm scoring functions as described in the above references are used to estimate the binding affinity of a ligand to a protein where it is already known that the ligand successfully binds to the protein and the protein/ligand complex has had its structure solved, the solved structure being present in the Protein Data Bank ("PDB"). Therefore, the scoring function has been developed with the benefit of known positive binding data. In order to allow for discrimination between positive and negative binders, a repulsion term must be added to the equation. In addition, a more satisfactory estimate of binding energy is achieved by computing the lipophilic interactions in a pairwise manner rather than using the area based energy term of the above Böhm functions. Therefore, in a preferred embodiment, the binding energy is estimated using a modified Böhm scoring function. In the modified Böhm scoring function, the binding energy between protein and ligand ($\Delta G_{bind}$) is estimated considering the following parameters: The reduction of binding energy due to the overall loss of translational and rotational entropy of the ligand ($\Delta G_0$); contributions from ideal hydrogen bonds ($\Delta G_{hb}$) where at least one partner is neutral; contributions from unperturbed ionic interactions ($\Delta G_{ionic}$); lipophilic interactions between lipophilic ligand atoms and lipophilic acceptor atoms ($\Delta G_{lipo}$); the loss of binding energy due to the freezing of internal degrees of freedom in the ligand, i.e., the freedom of rotation about each C—C bond is reduced ($\Delta G_{rot}$); the energy of the interaction between the protein and ligand ($E_{VdW}$). Consideration of these terms gives equation 1:

$$(\Delta G_{bind})=(\Delta G_0)+(\Delta G_{hb}\times N_{hb})+(\Delta G_{ionic}\times N_{ionic})+(\Delta G_{lipo}\times N_{lipo})+(\Delta G_{rot}+N_{rot})+(E_{VdW}).$$

Where N is the number of qualifying interactions for a specific term and, in one embodiment, $\Delta G_0$, $\Delta G_{hb}$, $\Delta G_{ionic}$, $\Delta G_{lipo}$ and $\Delta G_{rot}$ are constants which are given the values: 5.4, −4.7, −4.7, −0.17, and 1.4, respectively.

The term $N_{hb}$ is calculated according to equation 2:

$$N_{hb}=\Sigma_{h\text{-}bonds}f(\Delta R, \Delta\alpha)\times f(N_{neighb})\times f_{pcs}$$

$f(\Delta R, \Delta\alpha)$ is a penalty function which accounts for large deviations of hydrogen bonds from ideality and is calculated according to equation 3:

$$f(\Delta R, \Delta-\alpha)=f1(\Delta R)\times f2(\Delta\alpha)$$

Where: $f1(\Delta R)=1$ if $\Delta R<=\text{TOL}$ or $=1-(\Delta R-\text{TOL})/0.4$ if $\Delta R<=0.4+\text{TOL}$ or $=0$ if $\Delta R>0.4+\text{TOL}$ And: $f2(\Delta\alpha)=1$ if $\Delta\alpha<30°$ or$=1-(\Delta\alpha-30)/50$ if $\Delta\alpha<=80°$ or$=0$ if $\Delta\alpha>80°$ TOL is the tolerated deviation in hydrogen bond length=0.25 Å

ΔR is the deviation of the H—O/N hydrogen bond length from the ideal value=1.9 Å

Δα is the deviation of the hydrogen bond angle $\angle_{N/O-H\ldots O/N}$ from its idealized value of 180°.

$f(N_{neighb})$ distinguishes between concave and convex parts of a protein surface and therefore assigns greater weight to polar interactions found in pockets rather than those found at the protein surface. This function is calculated according to equation 4 below:

$$f(N_{neighb}) = (N_{neighb}/N_{neighb,0})^{\alpha} \text{ where } \alpha=0.5$$

$N_{neighb}$ is the number of non-hydrogen protein atoms that are closer than 5 Å to any given protein atom.

$N_{neighb,0}$ is a constant=25

$f_{pcs}$ is a function which allows for the polar contact surface area per hydrogen bond and therefore distinguishes between strong and weak hydrogen bonds and its value is determined according to the following criteria:

$$f_{pcs} = \beta \text{ when } A_{polar}/N_{HB} < 10\ \text{Å}^2$$

$$\text{or } f_{pcs} = 1 \text{ when } A_{polar}/N_{HB} > 10\ \text{Å}^2$$

$A_{polar}$ is the size of the polar protein-ligand contact surface $N_{HB}$ is the number of hydrogen bonds β is a constant whose value=1.2

For the implementation of the modified Böhm scoring function, the contributions from ionic interactions, $\Delta G_{ionic}$, are computed in a similar fashion to those from hydrogen bonds described above since the same geometry dependency is assumed.

The term $N_{lipo}$ is calculated according to equation 5 below:

$$N_{lipo} = \Sigma_{1L} f(r_{1L})$$

$f(r_{1L})$ is calculated for all lipophilic ligand atoms, 1, and all lipophilic protein atoms, L, according to the following criteria:

$$f(r_{1L})=1 \text{ when } r_{1L} <= R1\ f(r_{1L})=(r_{1L}-R1)/(R2-R1)$$
$$\text{when } R2 < r_{1L} > R1$$

$$f(r_{1L})=0 \text{ when } r_{1L} >= R2$$

Where: $R1 = r_1^{vdw} + r_L^{vdw} + 0.5$ and $R2 = R1 + 3.0$ and $r_1^{vdw}$ is the Van der Waal's radius of atom 1 and $r_L^{vdw}$ is the Van der Waal's radius of atom L

The term $N_{rot}$ is the number of rotable bonds of the amino acid side chain and is taken to be the number of acyclic $sp^3$-$sp^3$ and $sp^3$-$sp^2$ bonds. Rotations of terminal —$CH_3$ or —$NH_3$ are not taken into account.

The final term, $E_{VdW}$, is calculated according to equation 6 below:

$$E_{VdW} = \epsilon_1 \epsilon_2 ((r_1^{vdw} + r_2^{vdw})^{12}/r^{12} - (r_1^{vdw} + r_2^{vdw})^6/r^6),$$
where:

$\epsilon_1$ and $\epsilon_2$ are constants dependant upon atom identity $r_1^{vdw} + r_2^{vdw}$ are the Van der Waal's atomic radii r is the distance between a pair of atoms.

With regard to Equation 6, in one embodiment, the constants $\epsilon_1$ and $\epsilon_2$ are given the atom values: C: 0.245, N: 0.283, O: 0.316, S: 0.316, respectively (i.e. for atoms of Carbon, Nitrogen, Oxygen and Sulphur, respectively). With regards to equations 5 and 6, the Van der Waal's radii are given the atom values C: 1.85, N: 1.75, O: 1.60, S: 2.00 Å.

It should be understood that all predetermined values and constants given in the equations above are determined within the constraints of current understandings of protein ligand interactions with particular regard to the type of computation being undertaken herein. Therefore, it is possible that, as this scoring function is refined further, these values and constants may change hence any suitable numerical value which gives the desired results in terms of estimating the binding energy of a protein to a ligand may be used and hence fall within the scope of the present invention.

As described above, the scoring function is applied to data extracted from the database of side-chain conformations, atom identities, and interatomic distances. For the purposes of the present description, the number of MHC Class II molecules included in this database is 42 models plus four solved structures. It should be apparent from the above descriptions that the modular nature of the construction of the computational method of the present invention means that new models can simply be added and scanned with the peptide backbone library and side-chain conformational search function to create additional data sets which can be processed by the peptide scoring function as described above. This allows for the repertoire of scanned MHC Class II molecules to easily be increased, or structures and associated data to be replaced if data are available to create more accurate models of the existing alleles.

The present prediction method can be calibrated against a data set comprising a large number of peptides whose affinity for various MHC Class II molecules has previously been experimentally determined. By comparison of calculated versus experimental data, a cut of value can be determined above which it is known that all experimentally determined T-cell epitopes are correctly predicted.

It should be understood that, although the above scoring function is relatively simple compared to some sophisticated methodologies that are available, the calculations are performed extremely rapidly. It should also be understood that the objective is not to calculate the true binding energy per se for each peptide docked in the binding groove of a selected MHC Class II protein. The underlying objective is to obtain comparative binding energy data as an aid to predicting the location of T-cell epitopes based on the primary structure (i.e. amino acid sequence) of a selected protein. A relatively high binding energy or a binding energy above a selected threshold value would suggest the presence of a T-cell epitope in the ligand. The ligand may then be subjected to at least one round of amino-acid substitution and the binding energy recalculated. Due to the rapid nature of the calculations, these manipulations of the peptide sequence can be performed interactively within the program's user interface on cost-effectively available computer hardware. Major investment in computer hardware is thus not required. It would be apparent to one skilled in the art that other available software could be used for the same purposes. In particular, more sophisticated software which is capable of docking ligands into protein binding-sites may be used in conjunction with energy minimization. Examples of docking software are: DOCK (Kuntz et al., *J. Mol. Biol.*, 161:269–288 (1982)), LUDI (Böhm, H. J., *J. Comput Aided Mol. Des.*, 8:623–632 (1994)) and FLEXX (Rarey M., et al., *ISMB*, 3:300–308 (1995)). Examples of molecular modeling and manipulation software include: AMBER (Tripos) and CHARMm (Molecular Simulations Inc.). The use of these computational methods would severely limit the throughput of the method of this invention due to the lengths of processing time required to make the necessary calculations. However, it is feasible that such methods could be used as a 'secondary screen' to obtain more accurate calculations of binding energy for peptides which are found to be 'positive binders' via the method of the present invention. The limitation of processing time for sophisticated molecular mechanic or molecular dynamic calculations is one which is defined both by the design of the software which makes these calculations and the current technology limitations of computer hardware. It may be anticipated that, in the future, with the writing of more efficient code and the continuing increases in speed of computer processors, it may become feasible to make such calculations within a more manageable time-frame. Further information on energy functions applied to macromolecules and consideration of the various interactions that take place within a folded protein structure can be found in: Brooks, B. R., et al., *J. Comput. Chem.*, 4:187–217 (1983) and further information concerning general protein-ligand interactions can be found in: Dauber-Osguthorpe et al., *Proteins* 4(1):31–47(1988), which are incorporated herein by reference in their entirety. Useful background information can also be found, for example, in Fasman, G. D., ed., *Prediction of Protein Structure and the Principles of Protein Conformation*, Plenum Press, New York, ISBN: 0-306 4313-9.

The invention claimed is:

1. A modified murine EGF Receptor MAb 425 antibody including a VH variable region comprising an amino acid residue sequence selected from the group consisting of SEQ ID NO: 5, SEQ ID NO: 7, SEQ ID NO: 9, SEQ ID NO: 11, and SEQ ID NO: 13.

2. A modified murine EGF Receptor MAb 425 antibody including a VK variable region comprising an amino acid residue sequence selected from the group consisting of SEQ ID NO: 6, SEQ ID NO: 8, SEQ ID NO: 10, SEQ ID NO: 12, and SEQ ID NO: 14.

3. A modified murine EGF Receptor MAb 425 antibody including:

a VH variable region comprising an residue sequence selected from the group consisting of SEQ ID NO: 5, SEQ ID NO; 7, SEQ ID NO: 9, SEQ ID NO: 11, and SEQ ID NO: 13; and a VK variable region comprising an amino acid residue sequence selected from the group consisting of SEQ ID NO: 6, SEQ ID NO: 8, SEQ ID NO: 10, SEQ ID NO: 12, and SEQ ID NO: 14.

* * * * *